United States Patent
Georgakis (10) Patent No.: US 6,193,508 B1
(45) Date of Patent: Feb. 27, 2001

(54) SELF-LIGATING ORTHODONTIC BRACKET WITH ENHANCED ROTATION CONTROL

(75) Inventor: Evangelos G. Georgakis, Altaloma, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/276,060

(22) Filed: Mar. 25, 1999

(51) Int. Cl.⁷ .................................................. A61C 3/00
(52) U.S. Cl. ............................................................ 433/11
(58) Field of Search ...................... 433/11, 10, 13, 433/14

(56) References Cited

U.S. PATENT DOCUMENTS

| | | | |
|---|---|---|---|
| 3,772,787 | 11/1973 | Hanson | 32/14 |
| 4,103,423 | 8/1978 | Kessel | 32/14 |
| 4,149,314 | 4/1979 | Nonnenmann | 32/14 |
| 4,248,588 | 2/1981 | Hanson | 433/11 |
| 4,260,375 | 4/1981 | Wallshein | 433/11 |
| 4,371,337 | 2/1983 | Pletcher | 433/10 |
| 4,492,573 | 1/1985 | Hanson | 433/11 |
| 4,531,911 | 7/1985 | Creekmore | 433/8 |
| 4,559,012 | 12/1985 | Pletcher | 433/10 |
| 4,712,999 | 12/1987 | Rosenberg | 433/8 |
| 4,725,229 | 2/1988 | Miller | 433/11 |
| 5,067,897 | 11/1991 | Tuneberg | 433/8 |
| 5,094,614 | 3/1992 | Wildman | 433/14 |
| 5,269,681 | 12/1993 | Degnan | 433/11 |
| 5,322,435 | 6/1994 | Pletcher | 433/11 |
| 5,474,445 | * 12/1995 | Voudouris | 433/10 |
| 5,516,284 | 5/1996 | Wildman | 433/10 |
| 5,613,850 | 3/1997 | Wildman et al. | 433/10 |
| 5,630,715 | * 5/1997 | Voudouris | 433/8 |
| 5,685,711 | 11/1997 | Hanson | 433/11 |
| 5,711,666 | 1/1998 | Hanson | 433/11 |
| 5,857,849 | 1/1999 | Kurz | 433/10 |
| 5,857,850 | 1/1999 | Voudouris | 433/11 |
| 5,908,293 | 6/1999 | Voudouris | 433/10 |
| 5,967,773 | 10/1999 | Roman et al. | 433/11 |
| 5,971,753 | 10/1999 | Heiser | 433/11 |

FOREIGN PATENT DOCUMENTS

| | | | |
|---|---|---|---|
| 0 453 250 | 10/1991 | (EP) . | |
| WO98/20805 | 5/1998 | (WO) | A61C/7/28 |

* cited by examiner

*Primary Examiner*—John J. Wilson
*Assistant Examiner*—Melba Bumgarner
(74) *Attorney, Agent, or Firm*—James D. Christoff (57) ABSTRACT

An orthodontic bracket includes an archwire slot with mesial and distal end sections that present archwire relief areas. The bracket also includes a latch movable between a slot-open position in order to enable insertion or removal of an archwire, and a slot-closed position in order to retain an archwire in the archwire slot. The bracket includes at least one flange that extends along at least a portion of the mesial and distal archwire end sections and over a portion of the latch in order to provide enhanced rotational control over the underlying tooth without undue deformation of the latch.

11 Claims, 4 Drawing Sheets

SELF-LIGATING ORTHODONTIC BRACKET WITH ENHANCED ROTATION CONTROL

BACKGROUND OF THE INVENTION

1. Field of the Invention

The present invention broadly relates to brackets used in orthodontic treatment. More specifically, the present invention concerns orthodontic brackets that have a latch for releasably retaining an archwire in an archwire slot of the brackets.

2. Description of the Related Art

Orthodontic therapy is a specialized type of treatment within the field of dentistry, and involves movement of malpositioned teeth to orthodontically correct locations. Orthodontic treatment often improves the patient's occlusion and typically enhances the aesthetic appearance of the teeth.

Many types of orthodontic treatment programs involve the use of a set of tiny appliances and wires that are commonly known collectively as "braces". During such treatment programs, small appliances known as brackets are fixed to the patient's anterior, cuspid and bicuspid teeth, and an archwire is inserted into a slot of each bracket. The archwire forms a track to guide movement of the teeth to orthodontically correct locations. End sections of the archwires are typically captured in tiny appliances known as buccal tubes that are fixed to the patient's molar teeth.

Many types of orthodontic brackets have archwire slots that are open on one side for insertion of the archwire, and bounded on remaining sides by a central body of the bracket, by tiewings or by other structure. Brackets that are intended to be bonded to the patient's front tooth surfaces often have archwire slots that are open either on a buccolabial side (i.e., a side facing the patient's cheeks or lips) or an occlusal side (i.e., a side facing the outer tips of the teeth) of the archwire slot. Some brackets, however, are intended to be fixed to the lingual side of the patient's teeth (i.e., the side of the teeth facing the patient's tongue) and in that instance typically have an archwire slot that is open on a lingual side or on an occlusal side.

Many orthodontists use ligatures to connect the archwire to the brackets and to urge the archwire into an orientation of seating engagement in the archwire slot. One type of commercially available orthodontic ligature is a small, elastomeric O-ring. Orthodontic O-rings are installed by stretching the O-ring around small wings (known as "tiewings") that are connected to the bracket body on the gingival side (i.e., the side facing the patient's gingiva or gums) and on the occlusal side of the archwire slot. Once installed, the O-ring ligature extends around the tiewings as well as over the labial side of the archwire and urges the archwire toward a lingual wall of the archwire slot.

Metal ligatures, such as ligatures made of stainless steel, are also used to retain archwires in archwire slots of brackets. Metal ligatures are typically made of a short section of initially straight wire. During installation, the wire ligature is hooked around the tiewings and extended over the labial side of the archwire, and end sections of the ligature are then twisted together to form a loop to retain the ligature in place.

Unfortunately, some orthodontists are not entirely satisfied with elastomeric and metal ligatures. Such ligatures are somewhat time-consuming to install, both during initial installation and also during reinstallation whenever replacement of the archwire or ligatures is desired. As can be appreciated, a savings in the amount of time needed for ligation can help to reduce the total time that the practitioner must spend with the patient and consequently aid in reducing the overall costs of orthodontic treatment.

Other disadvantages are also associated with elastomeric and metal ligatures. For example, there have been reports that certain polyurethane elastomeric ligatures have exhibited deformation and force decay during the course of treatment. In some instances, elastomeric ligatures are stained by food and beverages consumed by the patient and become somewhat unsightly. Metal ligatures often have sharp ends that may retain plaque and food debris and also may increase the risk of infection.

In an effort to overcome the problems associated with conventional ligatures, a variety of orthodontic brackets have been proposed having various types of latches for coupling the archwire to the bracket. Such brackets are also known as self-ligating brackets. The latch comprises a clip, spring member, cover, shutter, bail or other structure that is connected to the bracket body for retaining an archwire in the archwire slot.

Examples of self-ligating orthodontic brackets having generally U-shaped ligating latch clips are described in U.S. Pat. Nos. 3,772,787, 4,248,588 and 4,492,573. In general, the clip of such brackets is slidably mounted on the bracket body, and a dental explorer or other small-tipped dental tool is used to move the clip relative to the body when needed in order to open or close the archwire slot. A self-ligating bracket known as the "Speed" brand bracket also has a movable, generally U-shaped clip for ligating the archwire to the bracket.

Other types of self-ligating brackets have latches that resemble swinging shutters or closures that pivotally move between a slot-open and a slot-closed position. For example, U.S. Pat. No. 4,712,999 has a rotatable cover plate that is pivotally connected at one end to a tiewing of the bracket along one side of the slot, and is releasably engagable at the other end with a tiewing that is located along the opposite side of the archwire slot. Other orthodontic brackets with swinging latches are described in U.S. Pat. Nos. 4,103,423, 5,516,284 and 5,685,711.

U.S. Pat. Nos. 4,371,337 and 4,559,012 describe self-ligating orthodontic brackets having latches that rotate about the longitudinal axis of the archwire slot. The latch of these references has a somewhat cylindrical shape and is rotatably received in a mating, cylindrical channel, and an outwardly extending arm is provided to assist in rotatably moving the latch between a slot-open and a slot-closed position.

A self-ligating orthodontic bracket that is described in U.S. Pat. No. 5,711,666 has a ligating latch that comprises a flexible flat spring member. One end of the spring member is fixed to the bracket body on one side of the archwire slot, and the opposite end of the spring member has notches that releasably engage latch sears or catches when the spring member is moved to a slot-closed position. To open the slot, the notches are disengaged from the catches and the spring member is bent to an orientation sufficient to enable the archwire to be removed from the archwire slot.

Other types of self-ligating orthodontic brackets have latches that comprise essentially flat plates that are slidable between a slot-open and a slot-closed position. Examples of such construction are shown in U.S. Pat. Nos. 5,094,614, 5,322,435 and 5,613,850. In general, the sliding latches described in those references move in upright channels that are located buccolabially of the archwire slot.

Another type of self-ligating bracket that has been proposed in the past has a latch that is made of a section of wire material that functions similar to a bail. The orthodontic brackets described in U.S. Pat. Nos. 4,149,314, 4,725,229 and 5,269,681 have wire-like latches that swing between a slot-closed position and a slot-open position. The orthodontic bracket described in U.S. Pat. No. 4,260,375 has a wire latch that is slidable between a slot-open and a slot-closed position.

Many of the self-ligating brackets described above as well as commercially-available self-ligating brackets have structure that is intended to prevent unintentional movement of the latch. It is undesirable, for example, for the latch to accidentally move to a slot-open position during the course of treatment since the archwire may disengage the bracket once the slot has been opened. Once the archwire has separated from the bracket, control over movement of the associated tooth is temporarily lost. In such instances, the patient must return to the orthodontist's office so that the wire can be re-inserted in the archwire slot in order to resume treatment.

It is also often desired to restrain movement of the latch in an opposite direction in some manner so that the latch does not unintentionally detach from the body of the bracket when the latch is opened. For example, the orthodontist may move the latch of each bracket to a slot-open position during the course of treatment in order to replace the archwire with an archwire having different characteristics. If the latch becomes separated from the bracket body during such procedures, the practitioner must interrupt the procedure to retrieve the latch and replace it on the bracket body.

Many practitioners prefer self-ligating orthodontic brackets over brackets that are not self-ligating because the need to ligate each bracket with an initially separate elastomeric O-ring or a metal ligature wire can be avoided. However, conventional self-ligating orthodontic brackets are not entirely satisfactory because of the lack of optimal control over movement of the underlying teeth. During the course of treatment, it may be necessary to shift each tooth relative to adjacent teeth in order to provide an aesthetically pleasing result at the conclusion of treatment. Precise control over movement of the teeth is desirable so that each tooth can be shifted as needed to its exact, intended orientation and in proper orthodontic relation relative to other teeth in the oral cavity.

In general, there are three types of tooth movement that are important to orthodontic practitioners. Tipping movement is one such type of movement, and may be defined as pivotal movement of the long axis of a tooth in a mesial-distal direction. Another movement is torque movement, and can be defined as pivotal movement of the long axis of a tooth in a buccal-lingual direction. The third type of tooth movement is rotational movement, and can be defined as rotational movement of a tooth about its long axis.

An orthodontic bracket offering superior control over movement of teeth during the course of orthodontic treatment is described in U.S. Pat. No. 4,531,911. While the commercial embodiments of the inventions described in U.S. Pat. No. 4,531,911 have been commercially successful and received widespread acclaim, such brackets are not self-ligating and as a consequence do not provide the advantages of the self-ligating brackets described above. U.S. Pat. No. 5,857,850 describes a self-ligating bracket that incorporates concepts of U.S. Pat. No. 4,531,911, but also is not entirely satisfactory.

SUMMARY OF THE INVENTION

The present invention is directed to a self-ligating orthodontic bracket having a latch that provides superior control over movement of the underlying tooth. In brief, the bracket has a movable latch that extends along archwire relief areas or pockets when closed. Additionally, one or more flanges extend over a portion of the latch in regions along the archwire relief areas and are positioned to help ensure that the latch does not move outwardly in a buccolabial direction when closed.

In more detail, the present invention is directed in one aspect toward an orthodontic bracket that comprises a base, a body extending from the base and an archwire slot extending along the body. The archwire slot includes a mesial end section, a distal end section and an intermediate section between the mesial end section and the distal end section. The mesial end section and the distal end section each include an archwire relief area having a greater occlusal-gingival width than the occlusal-gingival width of the intermediate section. The bracket also includes a latch that is movable relative to the body. The latch is movable to a slot-open position to enable insertion or removal of an archwire. The latch is also movable to a slot-closed position in order to retain the archwire in the archwire slot. At least one flange is connected to the body and extends in a mesial-distal direction along at least a portion of the mesial end section and the distal end section and also extends over a portion of the latch in buccolabial relation to the latch when the latch is in the slot-closed position.

Another aspect of the invention is also directed toward an orthodontic bracket that comprises a base, a body extending from the base and an archwire slot extending along the body. The archwire slot includes a mesial end section, a distal end section and an intermediate section between the mesial end section and the distal end section. In this aspect, the mesial end section and the distal end section each include an archwire relief area having a greater labial-lingual depth than the labial-lingual depth of the intermediate section. The bracket also includes a latch that is movable relative to the body. The latch is movable to a slot-open position to enable insertion or removal of an archwire. The latch is also movable to a slot-closed position in order to retain the archwire in the archwire slot. At least one flange is connected to the body and extends in a mesial-distal direction along at least a portion of the mesial end section and the distal end section, and also extends over a portion of the latch in buccolabial relation to the latch when the latch is in the slot-closed position.

The archwire relief areas as described above provide enhanced control over rotational, tipping and torquing movements of the underlying teeth. Additionally, the flange or flanges help secure the latch when the latch is in the closed position. In instances where the teeth are severely malpositioned and the archwire exerts substantial force on the bracket, the flange or flanges help limit outward movement of the latch so that the latch is not unduly deformed and/or unintentionally shifted to a slot-open position.

An additional aspect of the invention is also directed toward an orthodontic bracket that includes a base and a body extending from the base. The bracket includes an archwire slot extending along the body in a generally mesial-distal direction. A pair of elongated cavities extend along at least a portion of the archwire slot and are located buccolabially of the archwire slot. One of the cavities extends along an occlusal side of the archwire slot and the other cavity extends along a gingival side of the archwire slot. The bracket also includes a latch that is received in the cavities for retaining an archwire in the archwire slot.

These and other aspects of the invention are described in more detail in the text that follows and are illustrated in the accompanying drawings.

DETAILED DESCRIPTION OF THE PREFERRED EMBODIMENTS

An orthodontic bracket 10 according to one embodiment of the invention is shown in FIGS. 1–4. The bracket 10 includes a base 12 that is adapted for direct bonding to a surface of the tooth. The base 12 is shown only in FIG. 2 and preferably has a compound contour that matches the convex shape of the tooth. Optionally, the base 12 is provided with grooves, undercuts, wire mesh, particulates, adhesive-promoting coatings or any combination thereof in order to enhance bonding of the bracket 10 to a tooth.

The bracket 10 also includes a body 14 that extends outwardly from the base 12. The body 14 can be integral with or initially separate from the base 12. A pair of spaced apart occlusal tiewings 16 and a pair of spaced apart gingival tiewings 18 are integrally connected to the body 14.

An archwire slot 20 extends generally in a mesial-distal direction along the body 14. The archwire slot 20 includes a mesial end section 22, a distal end section 24 and an intermediate section 26 located between the mesial end section 22 and the distal end section 24. The intermediate section 26 has a rectangular configuration in side view as can be observed, for example, by reference to FIGS. 3 and 4 and preferably has dimensions that are suitable for matingly receiving an archwire having a matching, rectangular cross-sectional configuration.

Figure 3:
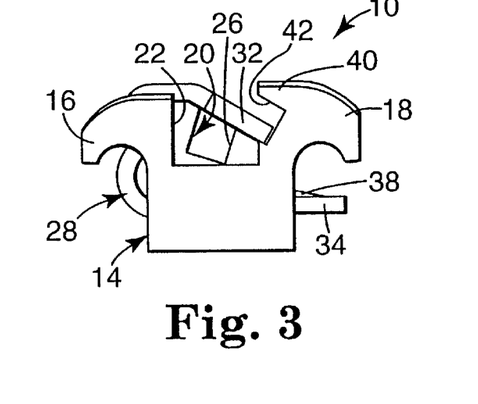
FIG. 3 is a side elevational view of the bracket illustrated in FIG. 1.
Figure 4:
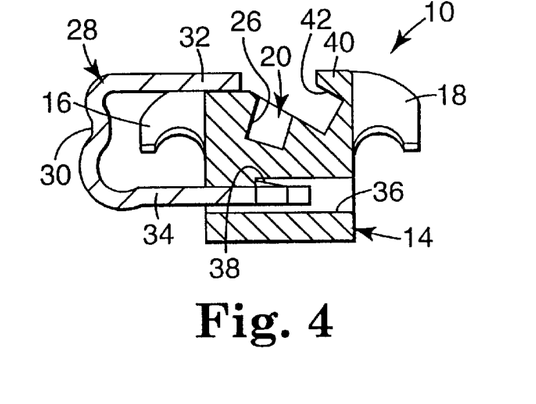
FIG. 4 is a side cross-sectional view of the bracket shown in FIG. 1 and taken along lines 4—4 of FIG. 1, except that the latch has been moved to a slot-open position.

Each of the archwire slot end sections 22, 24 presents a curved cutout or pocket that provides an archwire relief area. More specifically, each of the end sections 22, 24 has a width in an occlusal-gingival direction that is greater than the occlusal-gingival width of the intermediate archwire slot section 26. Additionally, each of the archwire slot end sections 22, 24 preferably has a labial-lingual depth that is greater than the labial-lingual depth of the intermediate archwire slot section 26.

The bracket 10 also includes a latch 28 that is movable relative to the body 14. In this embodiment, the latch 28 comprises a generally U-shaped, resilient spring clip having a central, occlusal recurve portion 30 as can be best appreciated by reference to FIG. 4. The latch 28 also includes a labial section 32 and a lingual section 34 which optionally has a length that is longer than the length of the labial section 32.

The body 14 also includes a rectangular channel 36 that extends in a generally occlusal-gingival direction. The channel 36 is located lingually of the archwire slot 20, and the lingual section 34 of the latch 28 is received in the channel 36. Although not shown in the drawings, in embodiments of the invention where the base 12 is initially separate from the body 14, the channel 36 is optionally located on a lingual wall of the body 14 to facilitate manufacture by a molding process, a milling process or the like, and the lingual side of the channel 36 is subsequently enclosed by the base 12 once the base 12 is connected to the body 14.

Figures 1, 2:
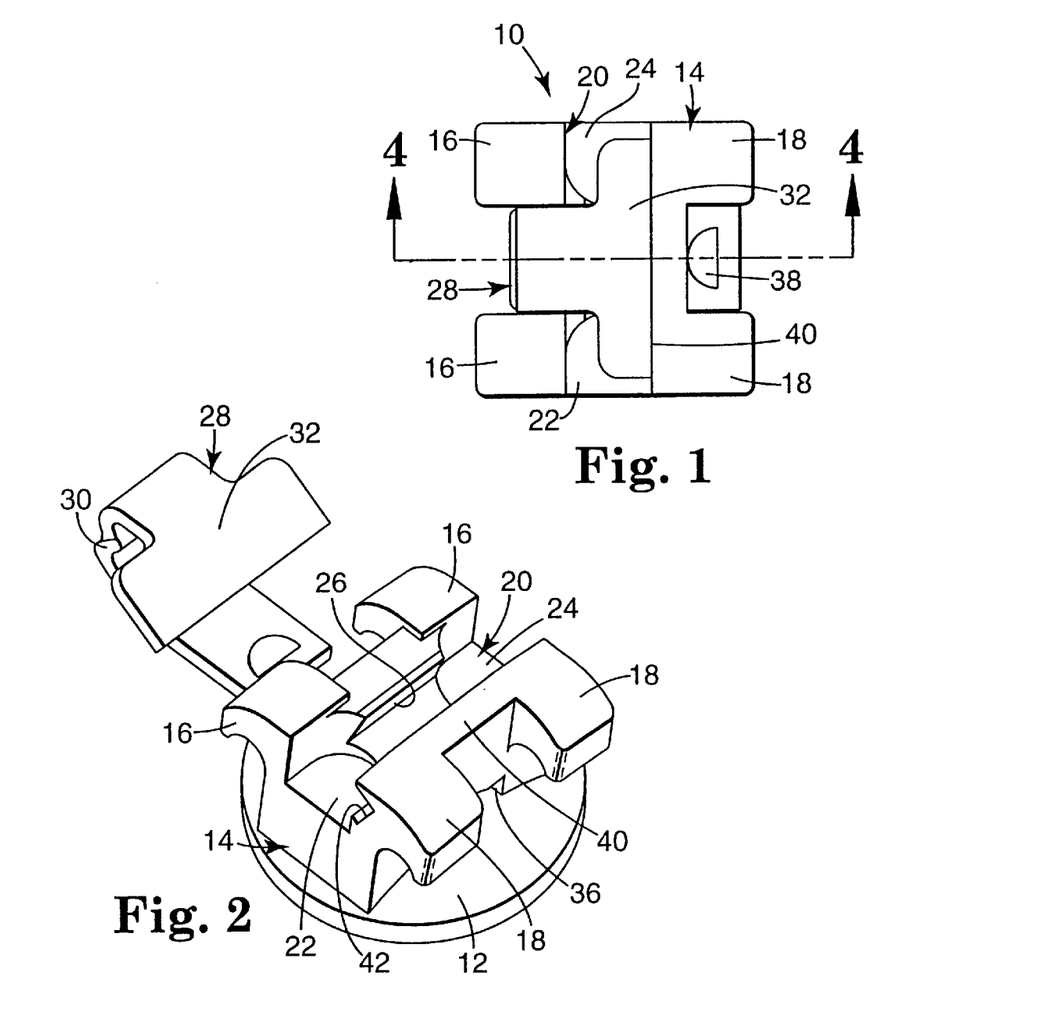
FIG. 1 is a front elevational view of a self-ligating orthodontic bracket constructed in accordance with one embodiment of the present invention, wherein a sliding latch of the bracket is shown in a slot-closed position.
FIG. 2 is a perspective view of the bracket shown in FIG. 1, except that the latch has been removed from a bracket body for purposes of illustration.

The latch 28 is movable relative to the body 14 in a generally occlusal-gingival direction. In FIGS. 1 and 3, the latch 28 is shown in a slot-closed position wherein the labial section 32 of the latch 28 extends over the archwire slot 20 and defines a buccolabial side of the latter.

FIG. 4 is an illustration of the latch 28 when moved to a slot-open position as might be used to permit insertion or removal of an archwire from the archwire slot 20. When the latch 28 is moved to the slot-open position, the labial section 32 of the latch 28 flexes outwardly and comes to rest upon a labial-facing surface of the occlusal tiewings 16.

The lingual section 34 of the latch 28 has a labially extending protrusion 38 that is optionally provided by punching or deforming a middle, gingival region of the lingual section 34. When the latch 28 is moved to the slot-open position, the protrusion 38 engages a shoulder in the channel 36 as shown in FIG. 4. The shoulder functions as a stop to limit further movement of the latch 28 in an occlusal direction. As such, the protrusion 38 substantially prevents the latch 28 from unintentionally separating from the body 14.

An elongated flange 40 is integrally connected to the body 14 and extends in a generally mesial-distal direction along the length of the archwire slot 20. Preferably, the flange 40 extends from a mesial side to a distal side of the bracket body 14 in continuous relation. However, the flange 40 could also be replaced with two, three or more flanges or protrusions that are separate and spaced apart from each other.

An elongated cavity 42 extends along a lingual side of the flange 40. The cavity 42 receives an outer gingival edge portion of the labial latch section 32 when the latch 28 is in the slot-closed position. Consequently, the flange 40 extends over a portion of the latch 28 in buccolabial relation to the latch 28 when the latter is in its slot-closed position.

The cavity 42 and the flange 40 serve as a stop to limit outward, buccolabial movement of the labial latch section 32 when the latch 28 is closed. Advantageously, the flange 40 extends along the mesial archwire slot end section 22 and the distal archwire slot end section 24 in order to substantially preclude bending or outward movement of the labial latch section 32 in areas next to the mesial or distal side of the bracket body 14.

For example, if the bracket 10 is bonded to a maloccluded tooth that is initially located a substantial distance in a lingual direction from adjacent teeth, an archwire that is received in the archwire slot 20 may, at least initially, place a substantial force in a labial direction on the labial latch section 32. The force on the labial latch section 32 in that instance might be greatest adjacent the mesial and distal sides of the bracket body 14. However, since the flange 40 extends across the gingival edge portion of the labial latch section 32 from its distal side and to its mesial side, the gingival edge portion of the latch 28 remains captured in the cavity 42 and does not unduly deform or bend, even in areas adjacent the mesial and distal sides of the bracket body 14. Such construction is an advantage in that the bracket 10 can be subjected to somewhat greater forces by an archwire during initial stages of treatment than would otherwise be possible.

If desired, the latch 28 may be removed from the body 14 during the course of treatment without detaching the bracket 10 from the underlying tooth. To remove the latch 28 from the body 14, the practitioner may insert a dental explorer or other fine-tipped dental instrument in the channel 36 and press the lingual latch section 34 in a lingual direction a distance sufficient to enable the protrusion 38 to clear the shoulder of the channel 36. The latch 28 can then be removed from the body 14 by moving the latch 28 in an occlusal direction. If desired, the bracket 10 can be used without the latch 28 in a manner similar to a conventional twin tiewing or single tiewing bracket, and conventional O-ring elastomeric ligatures or wire ligatures can be used in conjunction with the occlusal and gingival tiewings 16, 18 in order to ligate an archwire in the archwire slot 20.

During the course of treatment, the intermediate section 26 provides a precision active archwire slot constructed in accordance with edgewise orthodontic therapy techniques. Preferably, the archwire selected for edgewise therapy fits snugly in the archwire slot 20 in mating relation. The intermediate archwire slot section 26 allows the practitioner to control tipping, torque and rotational movements of the bracket 10 and consequently control corresponding movements of the underlying tooth as may be desired.

The archwire relief areas provided by the mesial and distal archwire slot end sections 22, 24 present inactive archwire reaction regions so long as the archwire does not flex sufficiently to engage the labial latch section 32 or the wall portions defining the end sections 22, 24. Consequently, the archwire relief areas provided by the mesial and distal archwire slot end sections 22, 24 effectively increase the interbracket width by preventing archwire interference in order to increase the available active length of the archwire between adjacent brackets.

The bracket body 14 may be made of any suitable material, such as metal, plastic or ceramic. Suitable metallic materials include series 300 stainless steels. The latch 28 is preferably made of a resilient metal or metallic alloy such as series 300 stainless steel. Optionally, the latch 28 may be made of a shape memory, superelastic alloy such as nitinol or beta titanium.

Figure 5:
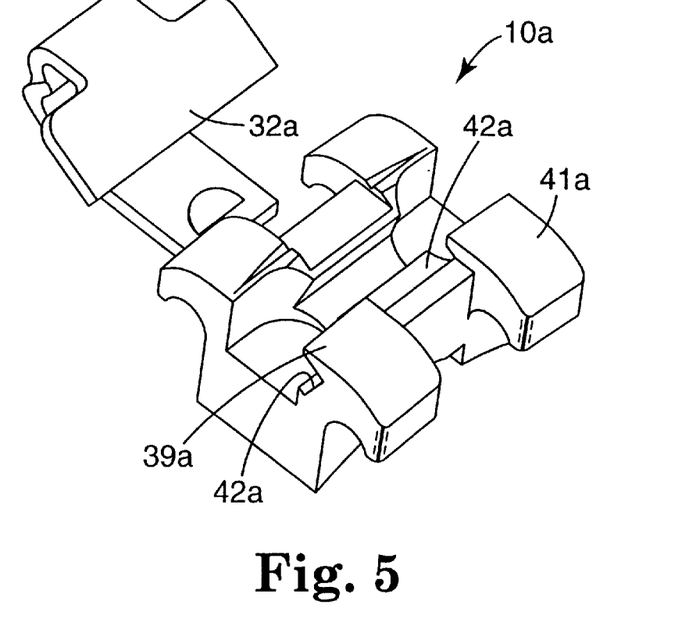
FIG. 5 is a perspective, exploded view somewhat similar to FIG. 2 but showing an orthodontic bracket according to another embodiment of the invention.

An orthodontic bracket 10a according to another embodiment of the invention is illustrated in FIG. 5. The bracket 10a is identical to the bracket 10 described above, except that the single flange 40 in FIGS. 1–4 has been replaced by two discrete, spaced apart flanges 39a, 41a in FIG. 5. The flange 39a is adjacent a mesial archwire slot end section 22a and the flange 41a is adjacent a distal archwire slot end section 24a.

A cavity 42a is presented beneath each of the flanges 39a, 41a. Each cavity 42a receives part of the gingival edge portion of a labial latch section 32a. The flanges 39a, 41a and the cavities 42a function in a manner similar to the function of the flange 40 and the cavity 42 described above. Remaining aspects of the bracket 10a are identical to the bracket 10 as set out above.

Figure 6:
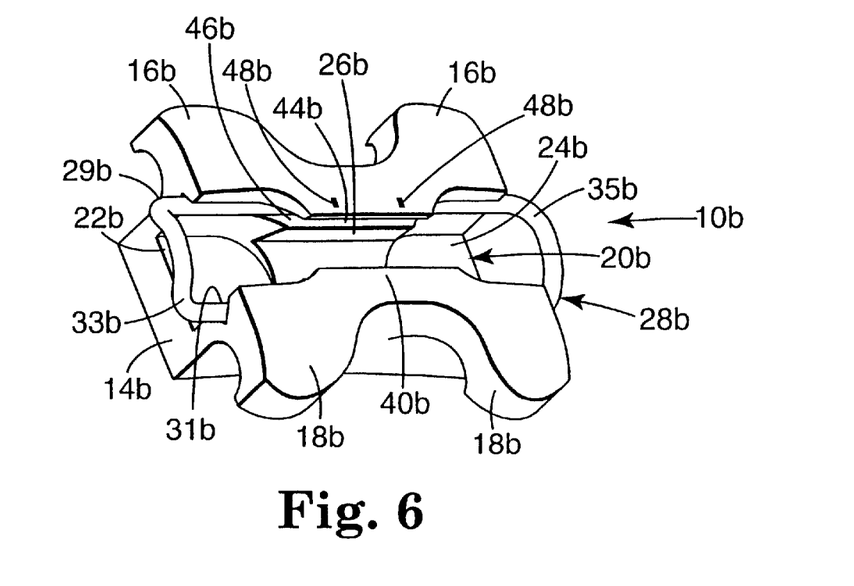
FIG. 6 is a perspective view of an orthodontic bracket according to yet another embodiment of the invention.
Figure 7:
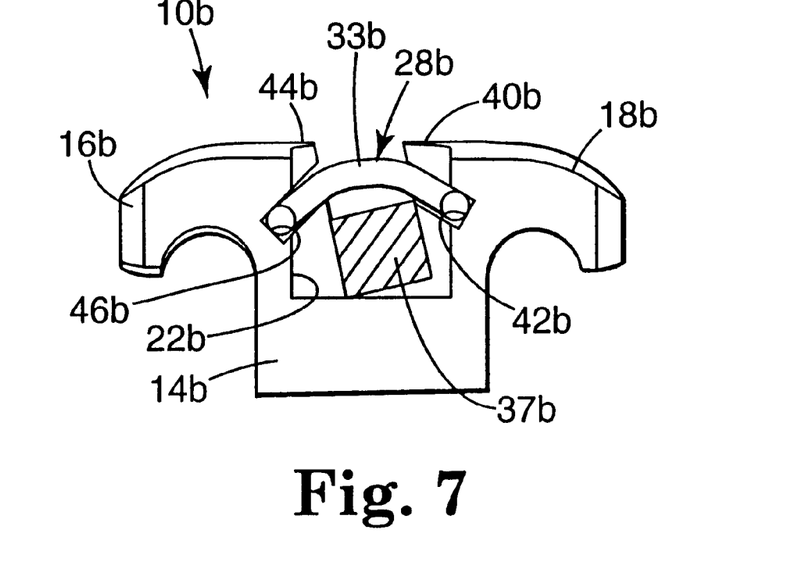
FIG. 7 is an end elevational view of the bracket depicted in FIG. 6.
Figure 8:
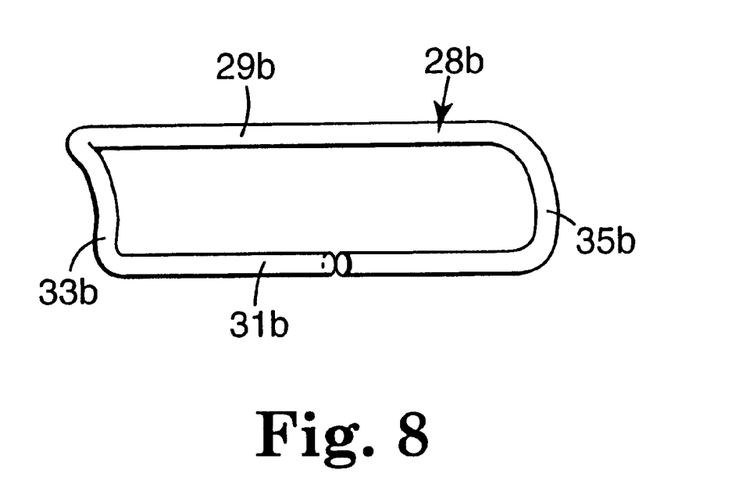
FIG. 8 is a perspective view of a latch alone of the bracket shown in FIGS. 6 and 7.

An orthodontic bracket 10b according to another embodiment of the invention is illustrated in FIGS. 6–8. The bracket 10b includes a body 14b and a base that is adapted to securely connect the body 14b to a tooth. The base is not shown in the drawings but is preferably identical or similar to the base 12 described above.

The bracket 10b includes a pair of occlusal tiewings 16b and a pair of gingival tiewings 18b. The bracket 10b also includes an archwire slot 20b having a mesial end section 22b, a distal end section 24b and an intermediate section 26b located between the mesial and distal end sections 22b, 24b. The archwire slot 20b (including the sections 22b, 24b, 26b) is preferably identical to the archwire slot 20 as described above.

The bracket 10b also includes a latch 28b that, in this embodiment, comprises a section of wire that has been formed or bent to present a loop. The latch 28b includes an occlusal section 29b that extends along the occlusal tiewings 16b and a gingival section 31b that extends along the gingival tiewings 18b. The occlusal section 29b and the gingival section 31b preferably extend in parallel relationship to each other.

The latch 28b also includes a mesial section 33b and a distal section 35b, both of which are curved outwardly in a buccolabially direction. The outwardly curved mesial and distal sections 33b, 35b have a shape sufficient to pass over a buccolabial side of an archwire 37b (shown in FIG. 7 only) when the archwire 37b is received in the archwire slot 20b. As shown in FIG. 8, the latch 28b is an open loop in that the gingival latch section 31b is not closed or continuous and presents two legs that are spaced apart from each other.

The bracket 10b has a gingival flange 40b that extends over a buccolabial side of a gingival cavity 42b. The bracket 10b also has an occlusal flange 44b that extends over a buccolabial side of an occlusal cavity 46b. The occlusal cavity 46b and the gingival cavity 42b each have a longitudinal axis that extends in a generally mesial-distal direction. Preferably, the flanges 40b, 44b and the cavities 42b, 46b extend along the entire mesial-distal extent of the archwire slot 20b including the sections 22b, 24b, 26b, although other constructions are also possible.

As illustrated in FIG. 6, the mesial latch section 33b preferably extends past the mesial side of the bracket body 14b in a mesial direction, and the distal latch section 35b preferably extends past the distal side of the bracket body 14b in a distal direction. Such construction is an advantage, in that enhanced control over rotational movements of the associated tooth is provided. As an alternative, however, the mesial section 33b and/or the distal section 35b could be located inwardly of the mesial and distal sides of the bracket body 14b.

Optionally, one of the flanges 40b, 44b is staked so that the latch 28b is captured in the underlying cavity. For example, the occlusal flange 44b may be pressed in a lingual direction in order to capture the occlusal section 29b of the latch 28b in the occlusal cavity 46b. In that embodiment, the occlusal flange 44b is preferably crimped or staked along the intermediate archwire section 26b at the locations designated 48b in FIG. 6. The staking is controlled so that the occlusal latch section 29b is non-releasably retained in the occlusal cavity 46b, but is not fixed relative to the body 14b in the occlusal cavity 46b. As a result, the latch 28b is free to pivot about the longitudinal axis of the occlusal latch section 29b in a curved arc relative to the body 14b when desired.

FIGS. 6 and 7 illustrate the latch 28b in a slot-closed position wherein the archwire 37b is retained in the archwire slot 20b. The latch 28b is also movable to a slot-open position when desired by releasing the gingival latch section 31b from the cavity 42b. To release the gingival latch section 31b from the cavity 42b, the latch 28b is moved along the cavities 42b, 46b in a mesial or distal direction until one of the two disconnected legs of the gingival section 31b is clear of the cavity 42b. Next, that leg is lifted in a buccolabial direction until it is past the labial face of the bracket body 14b in a labial direction and the latch 28b is then moved in an opposite (i.e., in a mesial or distal) direction while the lifted leg of the gingival section 31b slides across the labial face of the bracket body 14b. The latch 28b continues to be moved in that direction until the remaining leg of the gingival section 31b clears the cavity 42b, whereupon that leg is also lifted labially of the labial face of the bracket body 14b. At that time, the gingival latch section 31b is free of the gingival cavity 42b and the latch 28b pivots in the cavity 46b about the longitudinal axis of the occlusal latch section 29b to open the slot. The latch 28b may be moved to a slot-closed position when desired by reversing the sequence of those steps.

Preferably, the latch 28b is slidable along the cavities 42b, 46b in a mesial or distal direction to any one of a number of self-retained positions in use as chosen by the practitioner. Such sliding movement enables the latch 28b to be moved to an off-center position and vary the moment arm presented by the latch 28b. As a result, a choice of enhanced rotational control over movement of the underlying tooth is provided.

The latch 28b is preferably made from a shaped section of heat treated wire. Preferably, the wire may be made of a shape memory alloy such as nitinol or beta titanium. An example of a suitable wire diameter is 0.008 in. (0.4 mm).

The embodiment of the invention illustrated in FIGS. 6–8 is an advantage in that contact of the latch 28b with the archwire is minimal, resulting in a relatively low coefficient of friction between the bracket 10b and the archwire 37b. It is theorized that such a low coefficient of friction may facilitate sliding movement of the bracket 10b along the archwire 37b and as a consequence reduce the overall time needed to complete the orthodontic treatment program.

Figure 9:
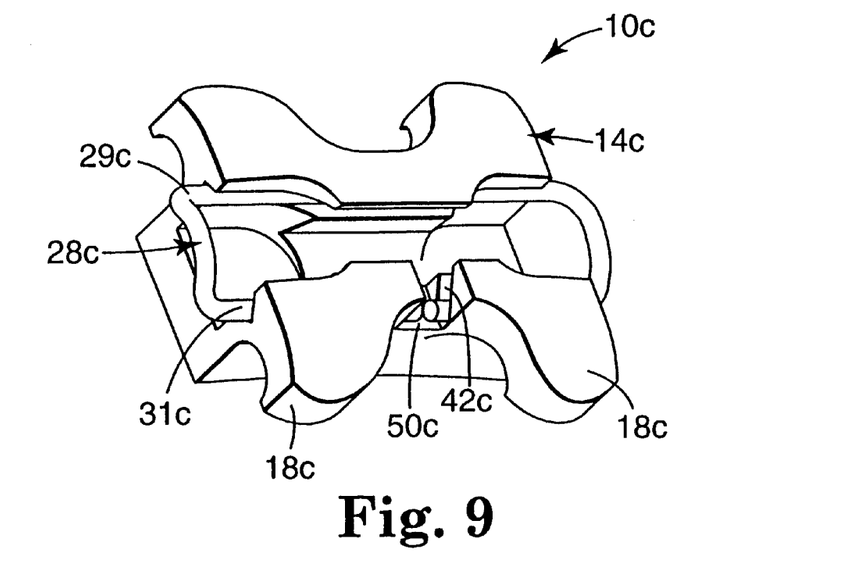
FIG. 9 is a view somewhat similar to FIG. 6 but in accordance with still another embodiment of the invention.

FIG. 9 is an illustration of an orthodontic bracket 10c according to another embodiment of the invention. Except as described below, the bracket 10c is essentially the same as the orthodontic bracket 10b discussed above and illustrated in FIGS. 6–8.

The bracket 10c includes a bracket body 14c having a notch 50c located between gingival tiewings 18c and adjacent a buccolabial face of the bracket body 14c. The notch 50c enables the practitioner to insert a fine-tipped hand instrument such as a dental explorer or probe on a gingival side of a wire latch 28c. The hand instrument is used to urge a gingival latch section 31c of the latch 28c in an occlusal direction in order to clear a gingival cavity 42c. Once the gingival latch section 31c is free of the gingival cavity 42c, the latch 28c may be pivoted about the longitudinal axis of an occlusal latch section 29c in order to move the latch 28c to a slot-open position.

To move the latch 28c to a slot-closed position, the latch 28c is pivoted in an opposite direction and the hand instrument is then used to deflect the gingival latch section 31c in an occlusal direction in order to enable the latch 28c to pivot to a fully closed position. Once the latch 28c is in a slot-closed position, the gingival latch section 31c is released and the inherent bias of the gingival latch section 31c causes the latter to spring back into the gingival cavity 42c in order to thereafter retain the latch 28c in the slot-closed position. Optionally, the practitioner's fingers may be used instead of a hand instrument in order to close the latch 28c and snap the gingival latch section 31c into the gingival cavity 42c.

In the embodiment shown in FIG. 9, the gingival latch section 31c is optionally closed as shown in the drawing so that a continuous loop is presented. Ends of the loop could be closed by any one of a number of suitable techniques, such as by a brazing or a welding operation. As an alternative, however, the gingival latch section 31c could be discontinuous and present two spaced-apart legs similar to the embodiment shown in FIG. 8.

Figure 10:
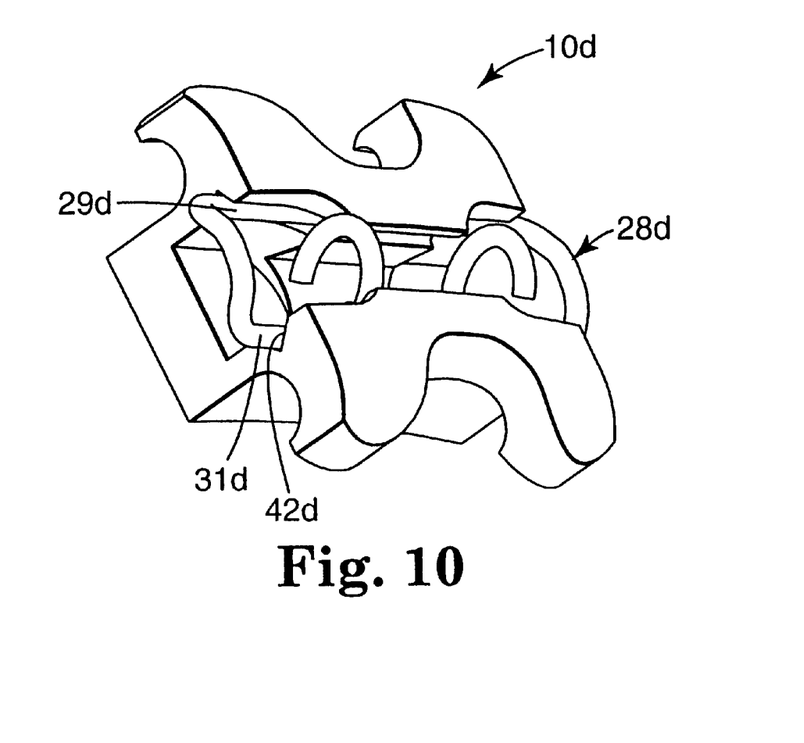
FIG. 10 is a view somewhat similar to FIG. 6 but showing an orthodontic bracket according to a further embodiment of the invention.

A self-ligating orthodontic bracket 10d constructed in accordance with another embodiment of the invention is illustrated in FIG. 10. The bracket 10d is essentially the same as the bracket 10b described above, except for the aspects set out in the following paragraphs.

The bracket 10d includes a latch 28d having an occlusal section 29d and a gingival section 31d. The gingival section 31d has two legs, each of which are bent in a curve to present a small hook or eyelet. The eyelets present a convenient opening for insertion of a fine-tipped hand instrument such as a dental explorer or probe.

The latch 28d is movable to a slot-open position in a manner similar to movement of the latch 28c described in connection with the bracket 10c shown in FIG. 9. However, a notch (such as notch 50c) need not be provided. Instead, the hand instrument is placed within the opening of the eyelets, which then function as a convenient handle for lifting each leg of the gingival latch section 31d from the gingival cavity 42d. Once each leg has been released from the gingival cavity 42d, the latch 28d is pivoted about the longitudinal axis of the occlusal latch section 29d in order to move the latch 28d to a slot-open position.

The latch 28d may be closed when desired by pivoting the latch 28d in an opposite direction and guiding the legs of the gingival latch section 31d into the gingival cavity 42d. Advantageously, the curved eyelets present a convenient, enlarged location for contact with the practitioner's finger so that the finger may be used to guide the legs of the gingival latch section 31d into the gingival cavity 42d. As an alternative, however, the hand instrument as described earlier can also be used in order to move the gingival latch section 13d into the gingival cavity 42d.

Many other variations of the invention are also possible. For example, the latch of FIGS. 6–10 could comprise a bail having a configuration other than the configuration shown in the drawings. Moreover, the latch in any of the embodiments could be a sliding plate or a pivotal cover having mesial and distal sections that extends over mesial and distal archwire relief areas and are adjacent one or more flanges to prevent undue or unintended outward movement in a buccolabial direction. As a consequence, the invention should not be deemed limited to the specific, presently preferred embodiments that are set out above in detail, but instead only by a fair scope of the claims that follow along with their equivalents.

What is claimed is:

1. An orthodontic bracket comprising:
   a base;
   a body extending from the base;
   an archwire slot extending along the body in a generally mesial-distal direction;
   a pair of cavities extending along at least a portion of the archwire slot and located buccolabially of the archwire slot, each of the cavities having a longitudinal axis that extends in a generally mesial-distal direction, one of the cavities extending along an occlusal side of the archwire slot and the other of the cavities extending along a gingival side of the archwire slot; and a latch received in the cavities for retaining an archwire in the archwire slot.

2. An orthodontic bracket according to claim 1 wherein the cavities extend in generally parallel relationship to each other from one side of the bracket to another.

3. An orthodontic bracket according to claim 1 wherein the latch comprises a section of wire.

4. An orthodontic bracket according to claim 3 wherein the wire has a loop-shaped configuration.

5. An orthodontic bracket according to claim 1 wherein the latch has a gingival portion and an occlusal portion, and wherein the latch is disconnected from the body by shifting at least one of the gingival portion and the occlusal portion toward the other.

6. An orthodontic bracket according to claim 1 wherein the bracket body includes a mesial side and a distal side, and wherein the latch extends past the mesial side in a mesial direction and also extends past the distal side in a distal direction.

7. An orthodontic bracket according to claim 1 wherein the latch is movable relative to the body in a generally mesial-distal direction.

8. An orthodontic bracket according to claim 1 wherein the latch is non-releasably retained in one of the cavities and is releasably retained in the other cavity.

9. An orthodontic bracket according to claim 1 wherein the latch is movable in a curved arc relative to the body to a slot-open position to enable insertion or removal of an archwire from the archwire slot.

10. An orthodontic bracket according to claim 1 wherein the latch comprises a section of wire, and wherein the wire includes an opposed pair of legs that are curved for reception of a hand instrument.

11. An orthodontic bracket according to claim 1 wherein the latch comprises a section of wire, and wherein the body includes a notch extending from a buccolabial face of the body to one of the cavities-in order to facilitate manipulation of the wire by a hand instrument.

* * * * *